United States Patent
Reams

(10) Patent No.: US 9,051,619 B2
(45) Date of Patent: Jun. 9, 2015

(54) METHODS AND COMPOSITIONS FOR PROSTATE CANCER METASTASIS

(75) Inventor: Romonia Renee Reams, Tallahassee, FL (US)

(73) Assignee: FLORIDA AGRICULTURAL AND MECHANICAL UNIVERSITY (FAMU), Tallahassee, FL (US)

( * ) Notice: Subject to any disclaimer, the term of this patent is extended or adjusted under 35 U.S.C. 154(b) by 200 days.

(21) Appl. No.: 13/428,750

(22) Filed: Mar. 23, 2012

(65) Prior Publication Data
US 2014/0248620 A1  Sep. 4, 2014

Related U.S. Application Data

(60) Provisional application No. 61/467,842, filed on Mar. 25, 2011.

(51) Int. Cl.
*G01N 33/53* (2006.01)
*C12Q 1/68* (2006.01)

(52) U.S. Cl.
CPC ........ *C12Q 1/6886* (2013.01); *C12Q 2600/118* (2013.01); *C12Q 2600/158* (2013.01)

(58) Field of Classification Search
CPC .............................. C12Q 1/6886; A61K 39/00
See application file for complete search history.

(56) References Cited

U.S. PATENT DOCUMENTS

2008/0064049 A1 * 3/2008 Clarke et al. .................. 435/7.23

OTHER PUBLICATIONS

Tockman et al (Cancer Res., 1992, 52:2711s-2718s).*

* cited by examiner

*Primary Examiner* — Sean Aeder
(74) *Attorney, Agent, or Firm* — Ballard Spahr LLP

(57) ABSTRACT

Provided are methods and compositions for determining an increased likelihood of prostate cancer cells in a subject to metastasize.

6 Claims, 6 Drawing Sheets

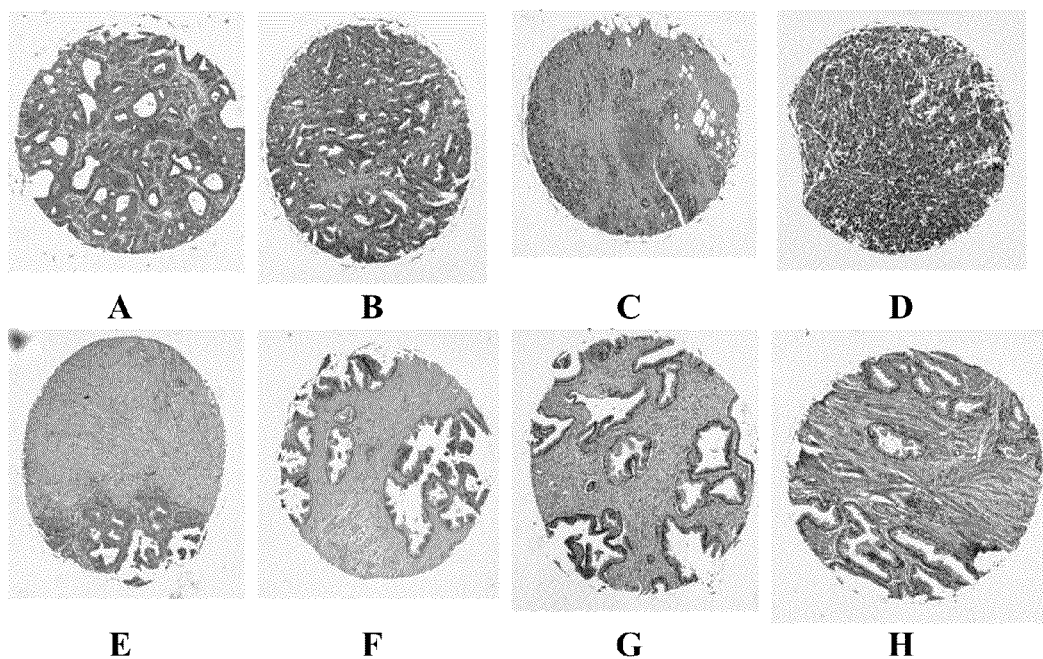
Figure 7 A-H

METHODS AND COMPOSITIONS FOR PROSTATE CANCER METASTASIS

CROSS-REFERENCE TO RELATED PATENT APPLICATIONS

This application claims the benefit of U.S. Provisional Patent Application No. 61/467,842, filed Mar. 25, 2011. The aforementioned application is herein incorporated by reference in its entirety.

STATEMENT OF GOVERNMENT RIGHTS

This invention was made with U.S. government support under DoD Contract #W81XWH-04-1-03-26. The government has certain rights in the invention.

FIELD OF THE INVENTION

The present invention relates to the use of a biological marker using RT-PCR to determine the metastatic potential of prostate cancer cells in a subject. Specifically, the present invention relates to the detection of overexpression of a gene found in prostate cancer cells in a subject to determine the likelihood that the prostate cancer cells will metastasize in the subject.

BACKGROUND OF THE INVENTION

Prostate cancer (CaP) is the second leading cause of cancer-related death among all men in the United States. However, incidence and mortality rates for this disease vary substantially among geographic areas and ethnic groups. Most notably African American (AA) men in the United States have the highest risk (19%) of developing prostate cancer, and due to the development of more aggressive disease, they have more than twice the mortality rate observed for other racial and ethnic groups[1]. The explanation for these differences is still unknown; however, proposed explanations include genetic factors, dietary factors, behavioral factors, biological tumor aggressiveness, socio-economic factors and gene-environment interaction[2-35]. While AA race/ethnicity is one of the three primary non-modifiable risk factors confirmed for CaP, there are only a few published cDNA microarray studies [36-38] that have focused on gene expression differences in AA tumors compared to gene expression in Caucasian American (CA) tumors in an attempt to understand prostate cancer health disparity.

SUMMARY OF THE INVENTION

Provided is a method of determining an increased likelihood of prostate cancer cells in a subject to metastasize, comprising detecting in a sample comprising prostate cancer cells from the subject over-expression of a nucleic acid of ABCD3 compared to expression levels of a nucleic acid of ABCD3 from a control sample, the over-expression of a nucleic acid of ABCD3 in prostate cancer cells being indicative of an increased likelihood of prostate cancer cells in the subject to metastasize.

Further provided is a method of determining an increased likelihood of prostate cancer cells in a subject to metastasize, comprising detecting in a sample from a subject an increased level of an ABCD3 polypeptide compared to the level of an ABCD3 polypeptide from a control sample, the increased level of an ABCD3 polypeptide in the sample from the subject being indicative of an increased likelihood of prostate cancer cells in the subject to metastasize.

DESCRIPTION OF THE DRAWINGS

FIG. 7 A-H shows expression of ABCD3 protein in human prostate tumor tissue (A-D), normal adjacent tissue (E-F) and normal or non-tumor prostate tissue (G-H).

DETAILED DESCRIPTION

Figure 1:
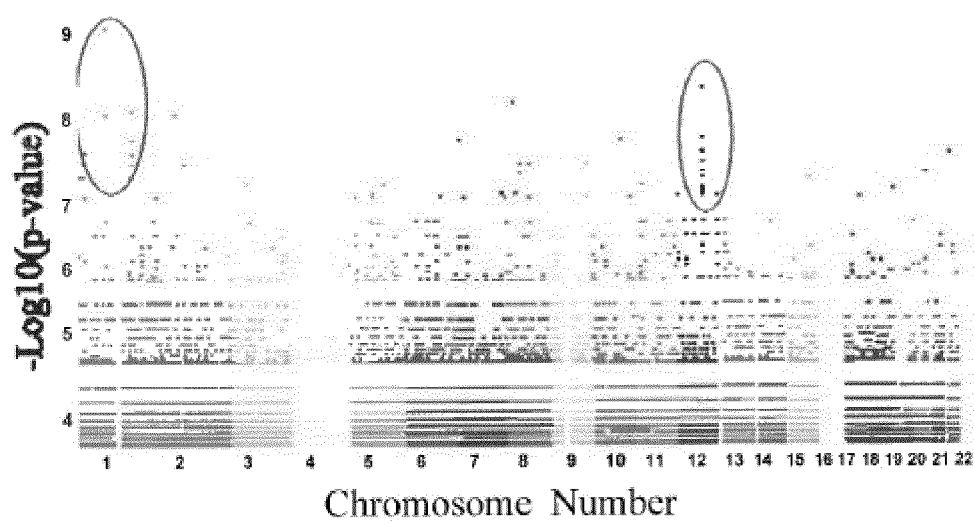
FIG. 1 shows results of genome-wide association SNPs with candidate prostate cancer genes using HapMap lymphoblastoid cell lines in YRI population. X-axis consists of different chromosomes and Y-axis consists of negative log p-value for association. This GWAS Plot of Gene-Gene Associations illustrates p-values (shown on y-axis) of SNP for gene variants found on chromosomes 1-22 (x-axis). The x-axis shows Chromosomes 1 through 22. Each dot represents gene variants or SNPs. In the circled dots to the extreme left positioned above Chromosome 1 (x-axis), the dot with the highest p-value represents an ABCD3 gene variant with a defined rs# that is strongly interacting with RANGAP1 to influence CaP tumors in African American men. All of the dots in the circle reveal an association of SNPs surrounding ABCD3 gene with basal gene expression of RanGAP1. This variation in gene expression RanGAP1 might be influenced by the SNPs in ABCD3. Similarly in the circled points to the far right, positioned above chromosome 12 (x-axis), the dot with the highest p-value represents the TMTC2 gene variant with a defined rs#, that strongly interacts with STXBP2. All the dots in the circle represent an association of SNPs surrounding TMTC2 gene with basal gene expression of STXBP2.

What is needed in the art are methods for determining whether prostate cancer cells in a subject have an increased likelihood of metastasizing compared to prostate cancer cells that have a low likelihood of metastasizing. Therefore, provided herein is the surprising discovery that the ABCD3 gene is over-expressed in subjects who have an increased likelihood of developing metastatic prostate cancer when compared to the expression of the ABCD3 gene in subjects who have either no prostate cancer or who have slow-growing, indolent prostate cancer that is unlikely to metastasize. It is contemplated that a person of skill in the art using the disclosed compositions and methods can detect over-expression of an ABCD3 nucleic acid and/or an abnormally elevated level of an ABCD3 polypeptide in a sample from a subject and thus determine that the subject has an increased likelihood of having or developing metastatic prostate cancer.

In order to determine a reasonably accurate prognosis and the best course of treatment for a subject diagnosed with prostate cancer, a person of skill, for example a physician, needs to know whether the cancer cells that were found in the sample from the cancerous prostate gland represented tumor cells that are slow-growing and unlikely to metastasize or cancer cells that are fast-growing and likely to metastasize. A subject whose prostate cancer comprises malignant cells that are slow-growing and unlikely to metastasize may be treated only with non-aggressive therapy, for example, observation, local radiation of the tumor, or surgical removal of the cancerous gland without adjunct therapy, such as radiation therapy and/or chemotherapy. In contrast, a subject whose prostate cancer comprises malignant cells that are fast-growing and likely to metastasize may be treated more aggressively, for example, with a combination of surgical removal of the subject's prostate gland, radiation, and/or chemotherapy.

The present discovery provides methods and compositions for a person of skill to determine whether a subject's prostate cancer has an increased likelihood of metastasizing that would require more aggressive therapy than if the prostate cancer comprised malignant cells unlikely to metastasize.

Therefore, disclosed is a method of determining an increased likelihood of prostate cancer cells in a subject to metastasize, comprising detecting in a sample comprising prostate cancer cells from the subject over-expression of a nucleic acid of ABCD3 compared to expression levels of a nucleic acid of ABCD3 from a control, the over-expression of a nucleic acid of ABCD3 in prostate cancer cells being indicative of an increased likelihood of prostate cancer cells in the subject to metastasize.

An example of a nucleic acid from a sample comprising prostate cancer cells is the ABCD3 gene. In one aspect, for example, a nucleic acid is an ABCD3 mRNA. It is contemplated that other nucleic acids that are now known or later to be found to be associated with prostate cancer can be used in the methods and compositions described herein.

In an aspect, a subject can be a mammal. In another aspect, the mammal can be human.

In one aspect, a sample can comprise prostate gland tissue comprising prostate cancer cells, which can be obtained, for example, when a person of skill, for example a physician, performs a biopsy of a subject's prostate gland. A biopsy of a prostate gland can be performed in various ways known in the art. For example, a physician can pass a needle into a prostate gland trans-rectally, trans-perineally, or trans-abdominally to obtain tissue for histopathological examination.

In another aspect, a sample can comprise prostate gland tissue comprising prostate cancer cells, which can be obtained, for example, as a surgical pathology specimen when a surgeon removes a subject's prostate gland during a surgical procedure known as a radical prostatectomy. A person of skill in the art, for example a surgical pathologist, using methods well known in the art, can examine a sample of prostate gland tissue obtained from a biopsy or surgical radical prostatectomy procedure to determine whether prostate cancer cells are present. The presence of prostate cancer cells in a sample confirms the diagnosis of prostate cancer in the subject.

In order to measure the level of expression of a nucleic acid, for example ABCD3, a person of skill can perform one or more assays on one or more biological samples. "Assaying," when used in reference to biological samples, preferably the cells in biological samples, refers to assessment or measurement of the presence and/or levels or concentrations of ABCD3 gene expression (transcripts or polypeptides) in the samples. This assessment is done by detecting and/or measuring the levels of RNA transcribed from the ABCD3 gene or polypeptides which are translated from the RNA transcripts.

With regard to elevated levels or elevated concentrations of one or more ABCD3 transcripts or polypeptides, "elevated" means an increase in the amount of the transcript or polypeptide in the test sample as compared to the control sample. "Elevated in the test sample as compared to the control sample" describes a situation where the presence of ABCD3 transcripts or polypeptides is detected in the test sample and the amount, level or concentration of the ABCD3 transcripts or polypeptides in the test sample is greater than in the control sample. This means that in the control sample, ABCD3 transcripts or polypeptides are either not detected, or that ABCD3 transcripts or polypeptides are detected but are not present in amounts, levels or concentrations as high as are present in the test sample.

Therefore, to ascertain whether the test sample contains "over-expressed" levels of ABCD3, a comparison of the levels in the test sample to the levels in one or more control samples is performed. Levels in a control sample or samples can be represented by a single value or range of values. Preferably, an average of the ABCD3 levels in more than one control sample is used for comparison with the ABCD3 levels in the test sample. More preferably, an average of the ABCD3 levels from a number of control samples sufficient to provide a statistically significant comparison with ABCD3 levels present in the test sample is used. The control sample levels of ABCD3 may be determined at the same time at which ABCD3 levels in the test sample are determined. The ABCD3 levels in the control samples may also be predetermined, meaning that the levels have been determined before the time at which ABCD3 levels in the test samples are determined. In the case where ABCD3 levels in control samples are predetermined, the values are preferably normalized or standardized such that they can be legitimately compared with values for ABCD3 levels in test samples that are determined later.

With reference to over-expressed, increased or elevated levels of ABCD3 transcripts or polypeptides in the test sample, the amount of the increase can be of various magnitudes. The increase may be relatively large. For example, a large increase could be a 100% or more increase in ABCD3 expression in the test sample as compared to the control sample. However, the increase may be relatively small. For example, the increase may be less than 100%, less than 50%, or even less than a 10% increase of the transcript or polypeptide in the test sample as compared to the control sample. Preferably, whatever the degree or magnitude of the increase, such increase is statistically significant. Methods for determining whether an increase is statistically significant are well known in the art of statistics and probability.

Comparison of the test sample to the control sample for the presence and/or levels of ABCD3 expression is used to determine the "aggressiveness" of the prostate cancer. A level of ABCD3 transcripts or polypeptides in the test sample that is higher than the level in the control sample indicates presence of an aggressive cancer that is likely to metastasize. The extent or degree of the increase between the level of ABCD3 transcripts or polypeptides in the test sample and the control sample correlates with the degree of aggressiveness of the tumor or cancer. "Aggressiveness" refers to the nature of tumor cell growth in a subject. For example, an aggressive prostate cancer has a higher probability of producing an unfavorable outcome in a patient than a cancer that is less aggressive. "Unfavorable outcome" refers to the probability that a subject will have a relatively short lifespan due to the aggressive nature of the cancer. Subjects with a less aggressive cancer or cancer that is not aggressive are expected to have a longer lifespan than a patient with an aggressive form of the cancer. In addition to predicting outcome in a subject, determination of ABCD3 over-expression and cancer aggressiveness is used for selecting an appropriate therapy for the subject with the prostate cancer.

In order to determine whether over-expression of ABCD3 is present in a sample of prostate cancer cells from a subject, provided is a composition comprising a pair of primers specific for ABCD3. A non-limiting list of primers that can be used in the disclosed methods includes siRNA ABCD3 gene part #4392421 Assay ID# s229943, Taqman primer part #4331182 Assay ID# Hs00161065_m1, and Taqman control part #4331182 Assay ID# Hs02758991_g1, which were obtained from Applied Biosystems.® Other primers known in the art to be capable of specifically amplifying the disclosed target nucleic acids can be used in the disclosed methods.

Disclosed are compositions including primers and probes, which are capable of interacting with the genes disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR. It is understood that in certain embodiments, the primers can also be extended using non-enzymatic techniques where, for example, the nucleotides or oligonucleotides used to extend the primer are modified such that they will chemically react to extend the primer in a sequence specific manner. Typically the disclosed primers hybridize with the nucleic acid or region of the nucleic acid or they hybridize with the complement of the nucleic acid or complement of a region of the nucleic acid.

The polynucleotides (primers or probes) can comprise the usual nucleotides consisting of a base moiety, a sugar moiety and a phosphate moiety, e.g., base moiety—adenine-9-yl (A), cytosine-1-yl (C), guanine-9-yl (G), uracil-1-yl (U), and thymin-1-yl (T); sugar moiety—ribose or deoxyribose, and phosphate moiety—pentavalent phosphate. They can also comprise a nucleotide analog, which contains some type of modification to either the base, sugar, or phosphate moieties. Modifications to nucleotides are well known in the art and would include for example, 5 methylcytosine (5 me C), 5 hydroxymethyl cytosine, xanthine, hypoxanthine, and 2 aminoadenine as well as modifications at the sugar or phosphate moieties. The polynucleotides can contain nucleotide substitutes which are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner but are linked together through a moiety other than a phosphate moiety. Nucleotide substitutes are able to conform to a double helix type structure when interacting with the appropriate target nucleic acid.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The primers for the target gene typically will be used to produce an amplified DNA product that contains a region of the target gene or the complete gene. In general, typically the size of the product will be such that the size can be accurately determined to within 3, or 2 or 1 nucleotides.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

The nucleic acids, such as the oligonucleotides to be used as primers, can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev.

Biochem. 53:323-356 (1984), (phosphotriester and phosphite-triester methods), and Narang et al., Methods Enzymol., 65:610-620 (1980), (phosphotriester method). Protein and nucleic acid molecules can be made using known methods such as those described by Nielsen et al., Bioconjug. Chem. 5:3-7 (1994).

The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23)12997-302 (1997), incorporated herein by reference.

Further disclosed are chips, for example microarray chips, where at least one address is a sequence or part of a sequence set forth in any of the nucleic acid sequences disclosed herein. For example, the chip can contain a probe for ABCD3.

Therefore, provided herein is an array comprising a substrate having a plurality of addresses, wherein each address comprises a capture probe that specifically binds under stringent conditions a nucleic acid of ABCD3. A nucleic acid bound by the capture probe of each address is unique among the plurality of addresses.

To create arrays, single-stranded polynucleotide probes can be spotted onto a substrate in a two-dimensional matrix or array. Each single-stranded polynucleotide probe can comprise at least 6, 7, 8, 9, 10, 11, 12, 13, 14, 15, 16, 17, 18, 19, 20, 25, or 30 or more contiguous nucleotides selected from the nucleotide sequences of a plurality of markers, for example the ABCD3 marker. The substrate can be any substrate to which polynucleotide probes can be attached including, but not limited to, glass, nitrocellulose, silicon, and nylon. Polynucleotide probes can be bound to the substrate by either covalent bonds or by non-specific interactions, such as hydrophobic interactions. Techniques for constructing arrays and methods of using these arrays are described in EP No. 0 799 897; PCT No. WO 97/29212; PCT No. WO 97/27317; EP No. 0 785 280; PCT No. WO 97/02357; U.S. Pat. Nos. 5,593,839; 5,578,832; EP No. 0 728 520; U.S. Pat. No. 5,599,695; EP No. 0 721 016; U.S. Pat. No. 5,556,752; PCT No. WO 95/22058; and U.S. Pat. No. 5,631,734. Commercially available polynucleotide arrays, such as Affymetrix® GeneChip™, can also be used. Use of the GeneChip™ to detect gene expression is described, for example, in Lockhart et al., Nature Biotechnology 14:1675 (1996); Chee et al., Science 274:610 (1996); Hacia et al., Nature Genetics 14:441, 1996; and Kozal et al., Nature Medicine 2:753, 1996.

Tissue samples can be treated to form single-stranded polynucleotides, for example, by heating or by chemical denaturation, as is known in the art. The single-stranded polynucleotides in the tissue sample can then be labeled and hybridized to the polynucleotide probes on the array. Detectable labels which can be used include, but are not limited to, radiolabels, biotinylated labels, fluorophors, and chemiluminescent labels. Double stranded polynucleotides, comprising the labeled sample polynucleotides bound to polynucleotide probes, can be detected once the unbound portion of the sample is washed away. Detection can be visual or with computer assistance.

Further provided is a method of determining an increased likelihood of prostate cancer cells in a subject to metastasize, comprising detecting in a sample from a subject an increased level of an ABCD3 polypeptide compared to the level of an ABCD3 polypeptide from a control, the increased level of ABCD3 polypeptide in the sample from the subject being indicative of an increased likelihood of prostate cancer cells in the subject to metastasize. Determining the amount of a disclosed polypeptide in a sample can refer to the steps that a person of skill would take to measure or ascertain some quantifiable value of the polypeptide in the sample. The art is familiar with the ways to measure an amount of the disclosed polypeptides in a sample. For example, an antibody that specifically binds an ABCD3 polypeptide can be used to identify and determine the level of an ABCD3 polypeptide in a sample from a subject for comparison to a level of ABCD3 polypeptide in a control.

The term "level" refers to the amount of a biomarker, for example ABCD3 or an ABCD3 polypeptide, in a sample obtained from an individual. The amount of the biomarker can be determined by any method known in the art and will depend in part on the nature of the biomarker (e.g., electrophoresis, including capillary electrophoresis, 1- and 2-dimensional electrophoresis, 2-dimensional difference gel electrophoresis DIGE followed by MALDI-ToF mass spectroscopy, chromatographic methods such as high performance liquid chromatography (HPLC), thin layer chromatography (TLC), hyperdiffusion chromatography, mass spectrometry (MS), various immunological methods such as fluid or gel precipitin reactions, single or double immunodiffusion, immunoelectrophoresis, radioimmunoassay (RIA), enzyme-linked immunosorbant assays (ELISA), immunofluorescent assays, Western blotting and others, and enzyme- or function-based activity assays. It is understood that the amount of the biomarker, for example ABCD3, need not be determined in absolute terms, but can be determined in relative terms. For example, the amount of the biomarker may be expressed by its concentration in a sample, by the concentration of an antibody that binds to an ABCD3 polypeptide, or by the functional activity (i.e., binding or enzymatic activity) of the biomarker (ABCD3 polypeptide).

For example, a tissue sample from a subject's prostate gland can be tested to determine whether there is an abnormally elevated level of an ABCD3 polypeptide by contacting the sample with an antibody that specifically binds and is directed to an ABCD3 polypeptide. By measuring the level of ABCD3 polypeptide in a tissue sample, for example prostate gland tissue, from the subject and comparing it to the level of ABCD3 polypeptide in a control, a person of skill can determine that the subject has an increased likelihood of having or developing metastatic prostate cancer if the level of ABCD3 polypeptide in the subject's sample is significantly higher than the level of ABCD3 polypeptide in the control.

In addition to prostate gland tissue, other body tissues can be used in the disclosed methods. For example, a person of skill can look for and detect over-expression of an ABCD3 nucleic acid and an ABCD3 polypeptide encoded by the ABCD3 nucleic acid by examining one or more body fluids from a subject and comparing the levels of the expressed ABCD3 nucleic acid and/or the ABCD3 polypeptide encoded by the ABCD3 nucleic acid. An increased level of ABCD3 nucleic acid and/or ABCD3 polypeptide in one or more body fluids of a subject compared to the level of ABCD3 nucleic acid and/or ABCD3 polypeptide in a control indicates that the subject has or may develop metastatic prostate cancer. Examples of body fluids include, but are not limited to, blood, plasma, serum, saliva, bile, feces, urine, perspiration, tears, aqueous humor, vitreous humor, mucus, semen, or cerebrospinal fluid.

Disclosed herein are kits that are drawn to reagents that can be used in practicing the methods disclosed herein. The kits can include any reagent or combination of reagents discussed herein or that would be understood to be required or beneficial in the practice of the disclosed methods. For example, the kits can include antibodies that specifically bind to an ABCD3 polypeptide and/or primers to perform the amplification reactions described, as well as the buffers and enzymes required to use the primers as intended. The kit can include instructions for using the reagents described in the methods disclosed herein.

DEFINITIONS AND NOMENCLATURE

The terminology used herein is for the purpose of describing particular embodiments only and is not intended to be limiting.

As used in the specification and the appended claims, the singular forms "a," "an," and "the" can include plural referents unless the context clearly dictates otherwise. Thus, for example, reference to "a nucleic acid" includes mixtures of nucleic acids, and the like.

The word "or" as used herein means any one member of a particular list and also includes any combination of members of that list.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint and independently of the other endpoint.

"Polypeptide" as used herein refers to any peptide, oligopeptide, polypeptide, gene product, expression product, or protein. A polypeptide is comprised of consecutive amino acids. The term "polypeptide" encompasses naturally occurring or synthetic molecules.

In addition, as used herein, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, yristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, "isolated polypeptide" or "purified polypeptide" is meant to mean a polypeptide (or a fragment thereof) that is substantially free from the materials with which the polypeptide is normally associated in nature. The polypeptides of the invention, or fragments thereof, can be obtained, for example, by extraction from a natural source (for example, a mammalian cell), by expression of a recombinant nucleic acid encoding the polypeptide (for example, in a cell or in a cell-free translation system), or by chemically synthesizing the polypeptide. In addition, polypeptide fragments may be obtained by any of these methods, or by cleaving full length proteins and/or polypeptides.

Also disclosed herein are isolated antibodies, antibody fragments and antigen-binding fragments thereof, that specifically bind to the ABCD3 polypeptide disclosed herein. Optionally, the isolated antibodies, antibody fragments, or antigen-binding fragment thereof can be neutralizing antibodies. The antibodies, antibody fragments and antigen-binding fragments thereof disclosed herein can be identified using the methods disclosed herein. For example, antibodies that bind to the polypeptides of the invention can be isolated using the antigen microarray described elsewhere herein.

The term "antibodies" is used herein in a broad sense and includes both polyclonal and monoclonal antibodies. In addition to intact immunoglobulin molecules, also disclosed are antibody fragments or polymers of those immunoglobulin molecules, and human or humanized versions of immunoglobulin molecules or fragments thereof, as long as they are chosen for their ability to interact with the polypeptides disclosed herein. "Antibody fragments" are portions of a complete antibody. A complete antibody refers to an antibody having two complete light chains and two complete heavy chains. An antibody fragment lacks all or a portion of one or more of the chains. Examples of antibody fragments include, but are not limited to, half antibodies and fragments of half antibodies. A half antibody is composed of a single light chain and a single heavy chain. Half antibodies and half antibody fragments can be produced by reducing an antibody or antibody fragment having two light chains and two heavy chains. Such antibody fragments are referred to as reduced antibodies. Reduced antibodies have exposed and reactive sulfhydryl groups. These sulfhydryl groups can be used as reactive chemical groups or coupling of biomolecules to the antibody fragment. A preferred half antibody fragment is a F(ab). The hinge region of an antibody or antibody fragment is the region where the light chain ends and the heavy chain goes on.

Antibody fragments for use in antibody conjugates can bind antigens. Preferably, the antibody fragment is specific for an antigen. An antibody or antibody fragment is specific for an antigen if it binds with significantly greater affinity to one epitope than to other epitopes. The antigen can be any molecule, compound, composition, or portion thereof to which an antibody fragment can bind. An analyte can be any molecule, compound or composition of interest. For example, the antigen can be a polynucleotide of the invention. The antibodies or antibody fragments can be tested for their desired activity using the in vitro assays described herein, or by analogous methods, after which their in vivo therapeutic or prophylactic activities are tested according to known clinical testing methods.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. Also disclosed are "chimeric" antibodies in which a portion of the heavy or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851 6855 (1984)).

Monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent.

Monoclonal antibodies may also be made by recombinant DNA methods, such as those described in U.S. Pat. No. 4,816, 567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, such as an Fv, Fab, Fab', or other antigen binding portion of an antibody, can be accomplished using routine techniques known in the art. For example, digestion can be performed using papain. Examples of papain digestion are described in WO 94/29348 published Dec. 22, 1994 and U.S. Pat. No. 4,342,566, the contents of which are hereby incorporated by reference in its entirety for its teaching of papain digestion of antibodies to prepare monovalent antibodies. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

Fragments, whether attached to other sequences, can also include insertions, deletions, substitutions, or other selected modifications of particular regions or specific amino acid residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86 95, 1991). Human antibodies (and fragments thereof) can also be produced using phage display libraries (Hoogenboom et al., J. Mol. Biol., 227:381, 1991; Marks et al., J. Mol. Biol., 222: 581, 1991).

Human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255 258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ line antibody gene array into such germ line mutant mice results in the production of human antibodies upon antigen challenge. Antibodies having the desired activity are selected using Env-CD4-co-receptor complexes as described herein.

Optionally, human antibodies can be made from memory B cells using a method for Epstein-Barr virus transformation of human B cells. (See, e.g., Triaggiai et al., An efficient method to make human monoclonal antibodies from memory B cells: potent neutralization of SARS coronavirus, Nat Med. 2004 August; 10(8):871-5. (2004)), which is herein incorporated by reference in its entirety for its teaching of a method to make human monoclonal antibodies from memory B cells). In short, memory B cells from a subject who has survived a natural infection are isolated and immortalized with EBV in the presence of irradiated mononuclear cells and a CpG oligonucleotide that acts as a polyclonal activator of memory B cells. The memory B cells are cultured and analyzed for the presence of specific antibodies. EBV-B cells from the culture producing the antibodies of the desired specificity are then cloned by limiting dilution in the presence of irradiated mononuclear cells, with the addition of CpG 2006 to increase cloning efficiency, and cultured. After culture of the EBV-B cells, monoclonal antibodies can be isolated. Such a method offers (1) antibodies that are produced by immortalization of memory B lymphocytes which are stable over a lifetime and can easily be isolated from peripheral blood and (2) the antibodies isolated from a primed natural host who has survived a natural infection, thus eliminating the need for immunization of experimental animals, which may show different susceptibility and, therefore, different immune responses.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323 327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522 525 (1986), Riechmann et al., Nature, 332:323-327 (1988), Verhoeyen et al., Science, 239: 1534 1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.). The antibodies disclosed herein can also be administered to a subject. Nucleic acid approaches for antibody delivery also exist. The broadly neutralizing antibodies to the polypeptides disclosed herein and antibody fragments can also be administered to subjects or subjects as a nucleic acid preparation (e.g., DNA or RNA) that encodes the antibody or antibody fragment, such that the subject's own cells take up the nucleic acid and produce and secrete the encoded antibody or antibody fragment.

As used herein, "specifically binds" is meant that an antibody recognizes and physically interacts with its cognate antigen (for example, a polypeptide encoded by the ABCD3 gene) and does not significantly recognize and interact with other antigens; such an antibody may be a polyclonal antibody or a monoclonal antibody, which are generated by techniques that are well known in the art.

The term "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "isolated nucleic acid" or "purified nucleic acid" is meant to mean DNA that is free of the genes that, in the naturally occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequence. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or polypeptide molecules.

As used herein, "probe," "primer," or oligonucleotide is meant to mean a single-stranded DNA or RNA molecule of defined sequence that can base-pair to a second DNA or RNA molecule that contains a complementary sequence (the "target"). The stability of the resulting hybrid depends upon the extent of the base-pairing that occurs. The extent of base-pairing is affected by parameters such as the degree of complementarity between the probe and target molecules and the degree of stringency of the hybridization conditions. The degree of hybridization stringency is affected by parameters such as temperature, salt concentration, and the concentration of organic molecules such as formamide and is determined by methods known to one skilled in the art. Probes or primers specific for nucleic acids capable of encoding the disclosed ABCD3 polypeptide (for example, genes and/or mRNAs) have at least 80%-90% sequence complementarity, preferably at least 91%-95% sequence complementarity, more preferably at least 96%-99% sequence complementarity, and most preferably 100% sequence complementarity to the region of the nucleic acid capable of encoding the disclosed ABCD3 polypeptide to which they hybridize. Probes, primers, and oligonucleotides may be detectably labeled, either radioactively, or non-radioactively, by methods well known to those skilled in the art. Probes, primers, and oligonucleotides are used for methods involving nucleic acid hybridization, such as: nucleic acid sequencing, reverse transcription and/or nucleic acid amplification by the polymerase chain reaction, single stranded conformational polymorphism (SSCP) analysis, restriction fragment polymorphism (RFLP) analysis, Southern hybridization, Northern hybridization, in situ hybridization, electrophoretic mobility shift assay (EMSA).

As used herein, "specifically hybridizes" is meant to mean that a probe, primer, or oligonucleotide recognizes and physically interacts (that is, base-pairs) with a substantially complementary nucleic acid (for example, a nucleic acid capable of encoding the disclosed ABCD3 polypeptide) under high stringency conditions, and does not substantially base pair with other nucleic acids.

As used herein, "high stringency conditions" is meant to mean conditions that allow hybridization comparable with that resulting from the use of a DNA probe of at least 40 nucleotides in length, in a buffer containing 0.5 M NaHPO4, pH 7.2, 7% SDS, 1 mM EDTA, and 1% BSA (Fraction V), at a temperature of 65° C., or a buffer containing 48% formamide, 4.8×SSC, 0.2 M Tris-Cl, pH 7.6, 1×Denhardt's solution, 10% dextran sulfate, and 0.1% SDS, at a temperature of 42° C. Other conditions for high stringency hybridization, such as for PCR, Northern, Southern, or in situ hybridization, DNA sequencing, etc., are well known by those skilled in the art of molecular biology. (See, for example, F. Ausubel et al., Current Protocols in Molecular Biology, John Wiley & Sons, New York, N.Y., 1998).

As used herein, "sample" is meant to mean a tissue or organ from an animal; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, plasma, serum, saliva, bile, feces, urine, perspiration, tears, aqueous humor, vitreous humor, mucus, semen, or cerebrospinal fluid) that contains cells or cell components.

As used herein, a "subject" is an individual. Thus, a subject can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and more preferably, a human. As used herein, the term "subject" is the same as "patient."

As used herein, "cancer" is meant to mean any of many diseases characterized by the presence of cancerous tissue in a subject. As used herein, "cancerous tissue" is meant to mean a tissue that comprises malignant neoplastic cells, exhibits an abnormal growth of cells and/or hyperproliferative cells. Cancerous tissue can be a primary malignant tumor, arising in a tissue or organ of origin, for example a prostate gland, or it can be a metastatic malignant tumor, growing in a body tissue which was not the source of the original tumor. Thus, malignant neoplastic cells can invade and destroy nearby tissue and spread to other parts of the body (metastasize). For example, primary prostate cancerous tissue comprises a tumor that is confined to a prostate gland and has not spread outside of the gland. In contrast, metastatic prostate cancerous tissue comprises prostate cancer cells that have spread outside of the gland to invade nearby pelvic organs and structures (local metastasis) and/or have spread to tissues and organs distant from the prostate gland (distant metastasis). As used herein, the term "neoplastic" means an abnormal growth of a cell or tissue (e.g., a tumor or non-solid hyper proliferative cellular activity) which may be benign or malignant (cancerous). As used herein, "abnormal growth of cells" and/or "hyperproliferative cells" are meant to refer to cell growth independent of normal regulatory mechanisms (e.g., loss of contact inhibition), including the abnormal growth of benign and malignant cells or other neoplastic diseases. As used herein, the term "tumor" includes neoplasms that are identifiable through clinical screening or diagnostic procedures including, but not limited to, palpation, biopsy, cell proliferation index, endoscopy, ultrasonography, computed tomography (CT), magnetic resonance imaging (MRI), positron emission tomography (PET), radiography, radionuclide evaluation, CT- or MRI-guided aspiration cytology, and imaging-guided needle biopsy, among others. Such diagnostic techniques are well known to those skilled in the art and are described in Holland, et al., Cancer Medicine, 4th Ed., Vol. One, Williams & Wilkins, Baltimore, Md. (1997).

As used herein, "prostate gland cancer" means cancer in/of the prostate gland of a subject and is interchangeable with "prostate cancer."

As used herein, "prostate cancer cells" are cells that comprise a prostate gland malignant tumor and may be cells in culture or cells sampled from tissue taken from the prostate gland of a subject.

As used herein, a "normal subject" is a subject who does not have prostate cancer.

As used herein, a "control" is a sample from either a normal subject or from non-cancerous tissue. A control may be a subject with a slow-growing, indolent prostate gland cancer that is unlikely to metastasize.

As used herein, "over-expression" means expression greater than the expression detected in normal, non-cancerous tissue or in tissue comprising a slow-growing prostate gland cancer. For example, a nucleic acid that is over-expressed may be expressed about 1 standard deviation above normal, or about 2 standard deviations above normal, or about 3 standard deviations above the normal level of expression. Therefore, a nucleic acid that is expressed about 3 standard deviations above a control level of expression is a nucleic acid that is over-expressed.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Elucidating genetic factors (variations and polymorphisms) in prostate cancer (CaP) tumors of AA may well explain prostate cancer disparity in African Americans (AA). To address the underlying genetic cause of prostate cancer burden in African Americans, a cohort of normal tumor paired samples from African American and Caucasian (CA) men that was previously obtained was looked at for differential gene expression within each group. In order to identify genetic variants associated with AA and gene expression pattern(s) unique to AA, a cDNA microarray project study was conducted that compared gene expression profiling in AA/CA tumors with a Gleason score six. Utilizing strict filtering criteria, over 97 differentially expressed genes were observed in the African American vs. Caucasian sample set [36] and identified 97 candidate genes that exhibited opposite gene expression polarity with respect to race groups; genes up-regulated in AA were simultaneously down-regulated in CA. (See 97 candidate genes below).

| GeneSymbol | | |
|---|---|---|
| WDR60 | GSCL | TRMT1 |
| TRPM7 | Up-ZNF443 | LOC285857 |
| DDX19B | CTNND1 | HOXB5 |
| REEP3 | FLJ30934 | ZFAND5 |
| CHRNA10 | SSH1 | C6orf105 |
| PITX1 | PDCD1 | SPATA12 |
| C9orf62 | cDNA on 13 | FLJ25476 |
| C21orf88 | ANK2 | LIPC |
| TTLL5 | TCTEK1D1 | SFRS1 |
| TCF12 | TPST1 | DIRAS2 |
| PGR | BUB3 | CSPP1 |
| MLL4 | DCAMK13 | DKFZp547J222 |
| NSFL1C | CPEB4 | ST6GALNAC3 |
| RNF168 | FLJ2078 | MTHFD2L |

-continued

| GeneSymbol | | |
|---|---|---|
| FLJ32658 | ARPC1A | LRRC28 |
| B1463184.1 | TMEM74 | DOT1L |
| GPC5 | TMEM67 | UBE2U |
| F111 | SLC6A15 | SLC4A9 |
| HNRPD | GSCL | A2BP1 |
| ADAMTS6 | Up-ZNF443 | NCR3 |
| MOBP | CTNND1 | GATA4 |
| RANGAPI | FLJ30934 | WDR1 |
| DLL3 | SSH1 | Up-GMR-7 |
| CXCL2 | PDCD1 | LOC731157 |
| GPR98 | cDNA on 13 | GPR12 |
| BUB3 | ANK2 | TPPP |
| DCAMK13 | TCTEK1D1 | C10orf53 |
| CPEB4 | TPST1 | BXDC2 |
| FLJ2078 | SLC13A2 | STXBP2 |
| ARPC1A | ZNF75 | FLJ44606 |
| TMEM74 | ITGB6 | GLUD1 |
| TMEM67 | HES4 | |
| SLC6A15 | DAD1 | |

Example 2 cDNA Microarray Prostate Candidate Gene List for AA Tumors

The gene list used to detect for gene-gene interactions in AA prostate tumors in African American males in the study described above was obtained from a previously published cDNA microarray study[36]. A cDNA microarray comparison study of prostate tumor gene expression in AA and CA was carried out[36]. To obtain differentially expressed genes or the gene list, four snap frozen tumors and four snap frozen non-tumor matched each, from AA and CA were used as controls. All tumors had a Gleason score of six. Gene expression profiles were measured for each of the micro-dissected CaP tumor samples using Affymetrix® U133A human arrays as described[36]. Each of the 8 prostate tumors and 8 matched controls underwent single hybridization and was arrayed individually (i.e., samples were not pooled). Data from the micro array CEL files were uploaded to R-Bioconductor for analysis. Gene changes were then obtained using Significance of Analysis of Microarrays (SAM) technique[53]. Normal AA tissue was paired to tumor AA, and normal CA was paired to tumor CA to generate for case paired t-tests for each race group; gene lists of differentially expressed genes in AA Tumor vs. AA controls and of CA Tumor vs CA controls were also generated. Differentially expressed genes that met the filtering criteria of a 4.0-fold change and a p<0.0001 were looked for. Neither the comparison of AA tumor to AA controls nor the comparison CA tumors to CA controls yielded genes that met both parts of these filtering criteria. However, when the ratio of CA tumor/CA normal to AA tumor/AA normal (case-matched ratios-race group tests for specific expression trends) was examined, 97 statistically significant, differentially expressed genes with 4-fold or greater fold change and p<0.0001 were identified. It was necessary to control for the high degree of genetic variation in AA tumor and AA non-tumor samples.

Example 3

Scan Database Analysis was Used to Look for Gene-Gene Interactions

SCAN is a large-scale database of genetics and genomics data associated to a web-interface and a set of methods and algorithms that can be used for mining the data in it. Information on the relationship between SNPs and expression transcript levels (eQTLs) that is served by SCAN comes from a series of publications describing studies characterizing eQTLs in lymphoblastoid cell lines from HapMaP Caucasian (CEU) and Yoruba (YRI) samples for which transcript levels have been assayed using the Affymetrix® Human Exon 1.0 ST Array[39-44].

The SCAN database contains two categories of SNP annotations: (1) Physical-based annotation or SNPs categorized according to their position relative to genes (intronic, intergenic, etc.) and according to linkage dysequilibrium (LD) patterns (an inter-genic SNP can be annotated to a gene if it is in LD with variation in the gene). (2) Functional annotation where SNPs are classified according to their effects on expression levels, i.e., whether they are eQTLs for that gene. Information on physical, functional and LD annotation served on the SCAN database comes directly from public resources, including HapMap (release 23a), NCBI (dbSNP 129), or is information created by using data downloaded from these public resources. In SCAN database, genotype data for the YRI samples were obtained from HapMap project (http://www.hapmap.org). Genotype and gene annotations were obtained from NCBI, dbSNP 129.

Appropriate gene identifiers for the prostate candidate genes were uploaded and queried for SNPs that are significantly associated with expression of prostate candidate genes in Yoruba (YRI) population in lymphoblastoid cell lines. The SCAN analysis output reports a list of SNPs in gene(s) that predict expression quantitative trait loci found in mRNA profiles from YRI with p-values less than 0.0001.

Example 4

Hugo Gene Symbols

To enter a list of genes into SCAN, it is first necessary to use the HUGO (Human Genome Organization) gene symbol—the unique gene name and symbol given to each human gene by The HUGO Gene Nomenclature Committee (HGNC). HUGO gene symbols for 85 of the 97 genes (hereafter referred to as 85/97) were identified (Table 1).

Example 5

Scan Database SNP and Expression Transcript Level Association Results

After uploading the 85/97 prostate candidate genes with appropriate HUGO gene symbols and querying for SNPs in the 85/97 significantly associated with SNPs in the Hap Map Yoruba (YRI) population, approximately 26527 genotype-phenotype associations were obtained with a p-value $<10^{-3}$, of which 17542/26527 associations had a p-value $<10^{-4}$.

SNPs and expression transcript level (eQTL) association results identified two gene=gene associations. Association results in lymphoblastoid cell lines showed that expression of RanGAPl gene which is a key regulator of the RAN GTP/GDP cycle, located on chromosome 22, may be involved with several SNPs in ABCD3 gene which is ATP-Binding cassette, subfamily member that is located on chromosome 1 (shown as encircled dots on far left in FIG. 1). In addition, expression of STXBP2 gene which is a syntaxin-binding protein that is located on chromosome 19 may be involved with a region on chromosome 12. The chromosome 12 region consists of transmembrane and tetratricopeptide repeat containing 2 (TMTC2) gene that is approximately 400 kb away from the region where STXBP2 gene is associated (shown as encircled dots on far right of FIG. 1). Genome-wide results also showed that there were 1167 cis interactions (where expression gene and SNP are located on the same chromosome) out of 26527 associations with a p-value <$10^{-3}$. Most of the cis-regulatory associations were found in protein coding regions.

Example 6

CaP Candidate Genes Found in Erk, Mapk, Nfkb Pathways

To further substantiate the link of ABCD3 with other cell signaling molecules that contribute to prostate cancer, an indirect in silico ingenuity pathway analysis was utilized.

Pathway analysis was performed in an attempt to define biological relationships among candidate genes identified during the study using the genes that are involved with the downstream effects of SNPs along with the 85/97 candidate prostate cancer genes as described above. Ingenuity Pathway Analysis (IPA) (see ingenuity.com) was used to perform the pathway analysis. This software consists of a curated database and several analysis tools to determine the probability of finding a set of genes within annotated pathway or network annotation. Other similar analysis tools can be used.

Ingenuity software calculates p-value for the probability of finding a set of genes within a given pathway. Fisher's exact test was used to calculate the p-values associated with finding 536 candidate prostate genes obtained during this study (which includes 85/97 candidate genes from a previous differential expression study[36] and 451 candidate genes as discussed above that correspond to Cis-regulatory SNPs that are significantly associated with the 85 candidate genes) within an annotated network from Ingenuity Knowledge Base.

Figure 2:
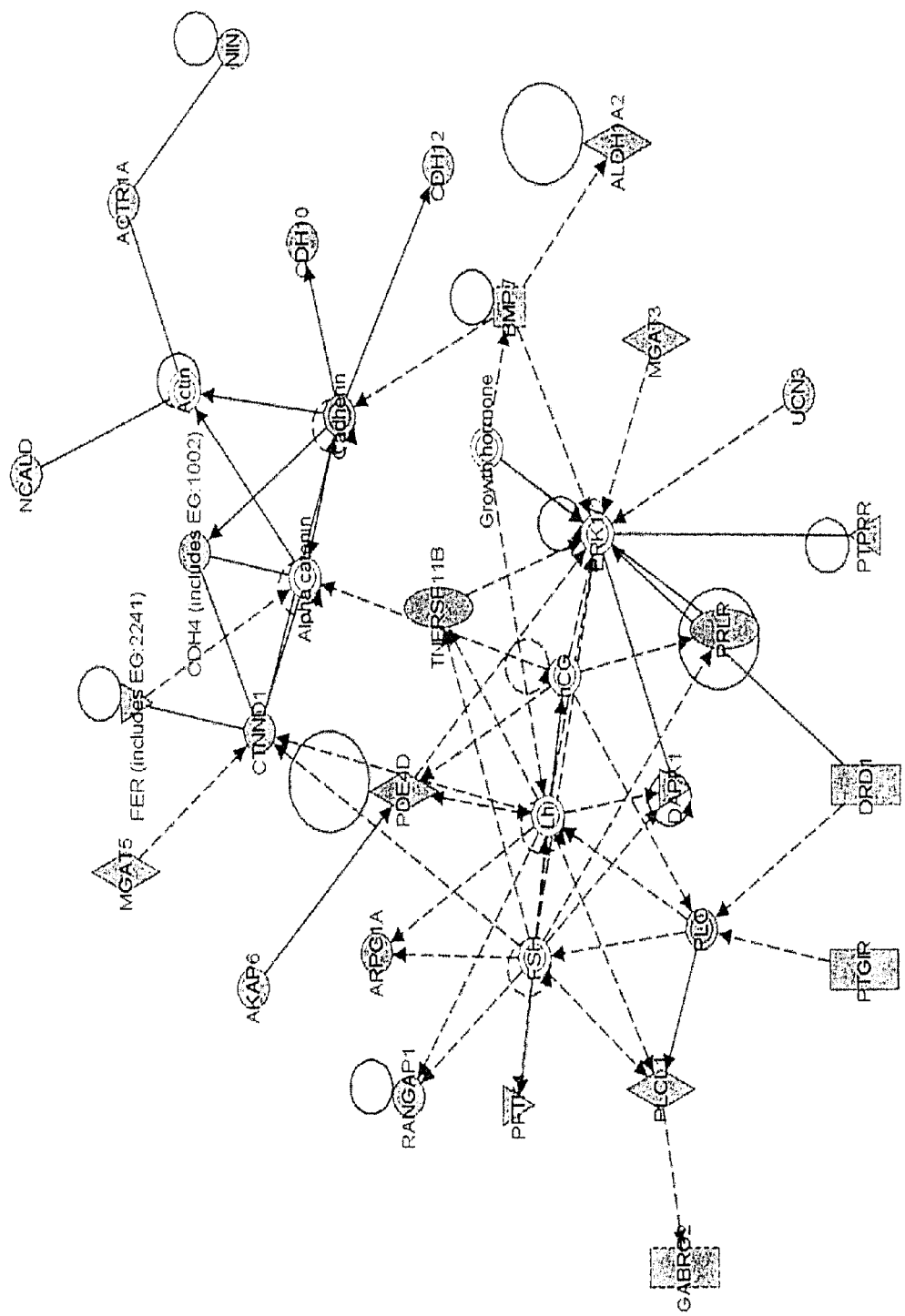
FIG. 2 shows Network1, top network from the network analysis with the list of genes that were associated with the downstream of cis interaction SNPs using Ingenuity Pathway Analysis. Dotted line indicates an indirect connection, and solid lines indicate a direction interaction between genes.
Figure 3:
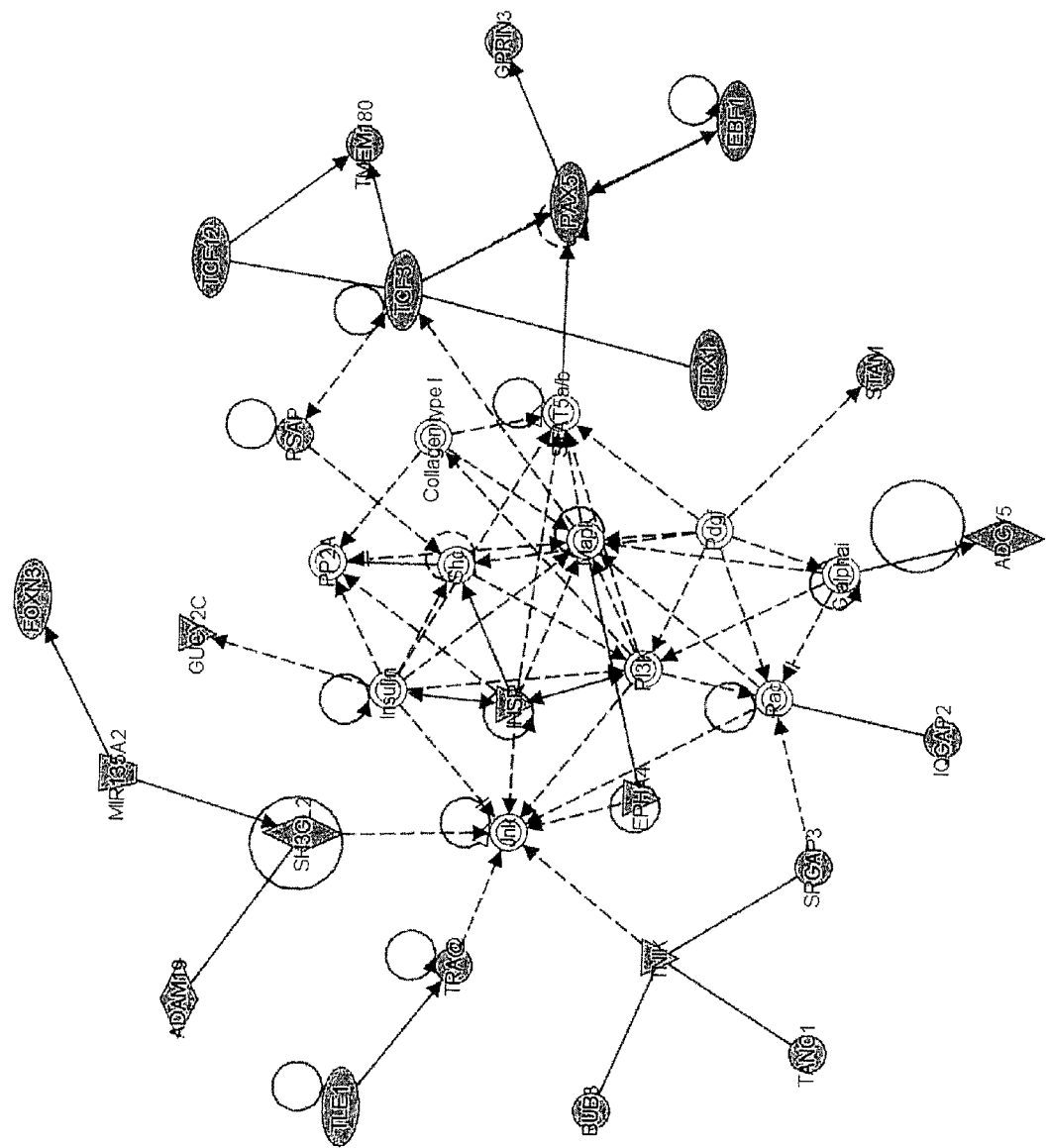
FIG. 3 shows Network2, top second network from Ingenuity Pathway Analysis. Dotted line indicates an indirect connection and solid lines indicate a direction interaction between genes.
Figure 4:
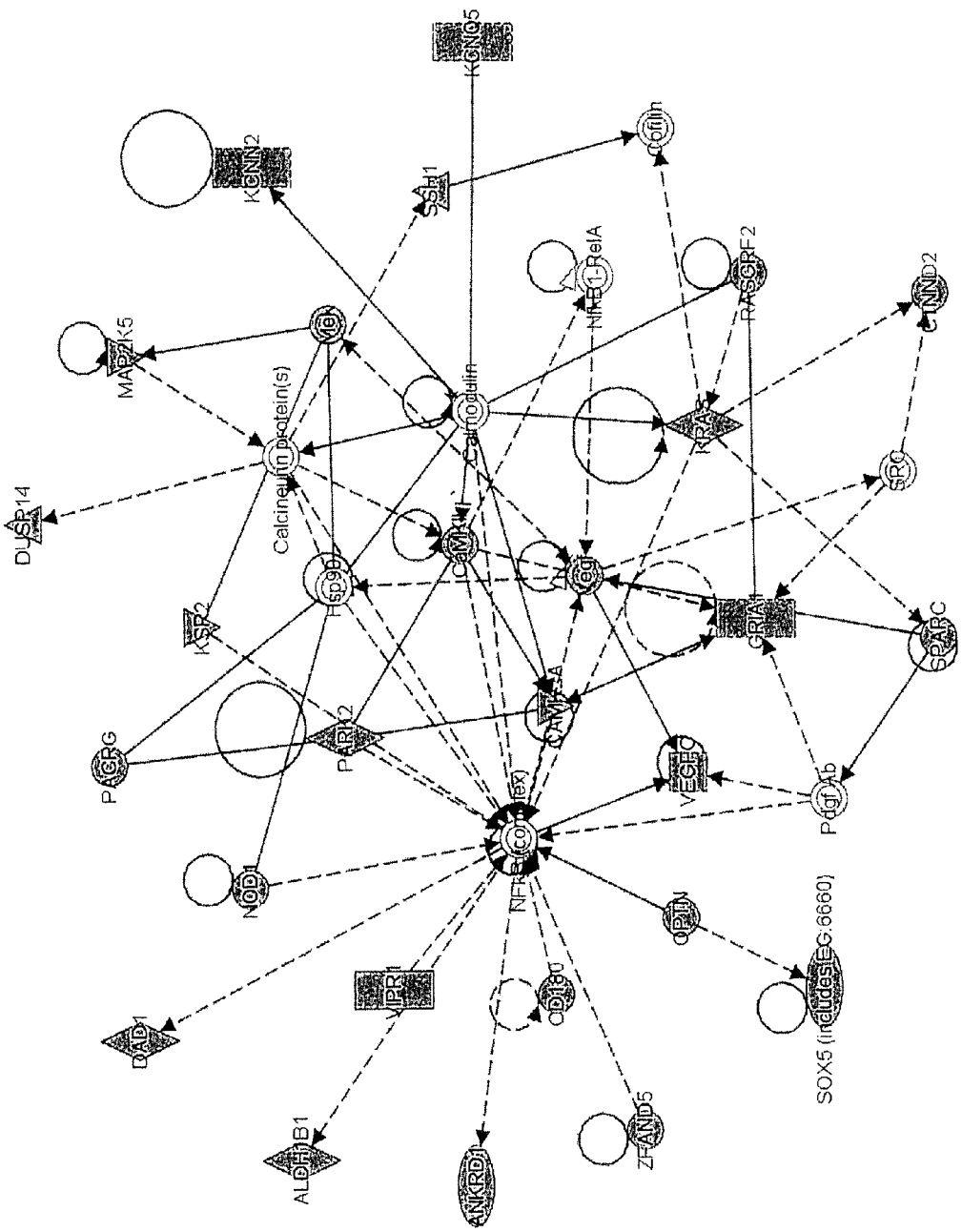
FIG. 4 shows top third network from the list of genes that were associated with the downstream of cis interaction SNPs using Ingenuity Pathway Analysis. Dotted line indicates an indirect connection and solid lines indicate a direction interaction between genes.

Results showed a high probability for finding candidate genes in three network hubs centered on ERK, MAPK and NFkB pathways (shown in FIGS. 2, 3 and 4, respectively). In FIG. 2 the Ingenuity Pathway Analysis identified ERK as the Top network signaling Hub where the shaded shapes indicate the candidate genes from the present study. RANGAP1 is found in the ERK pathway. Dotted line indicates an indirect cellular interaction and solid lines indicate a physical interaction between genes. Genes are identified with their HUGO symbol. Dotted line indicates an indirect cellular interaction, and solid lines indicate a physical interaction (acts on or inhibits) between genes. Different shapes (diamond, circle or rectangles) of the nodes represent functional classification of the genes.

In FIG. 3 the Ingenuity Pathway Analysis identified MapK as second Top network signaling Hub where the shaded shapes indicate the candidate genes from the current study. Dotted line indicates an indirect cellular interaction and solid lines indicate a physical interaction between genes. Molecules are identified with their HUGO symbol. Different shapes (diamond, circle or rectangles) of the nodes represent functional classification of the genes shown.

In FIG. 4 the Ingenuity Pathway Analysis identified NFKB as the Top Network signaling Hub where the shaded shapes indicate the candidate genes from the present study. Dotted line indicates an indirect cellular interaction and solid lines indicate a physical interaction (i.e., binding) between genes. Molecules are identified with their HUGO symbol. Different shapes (diamond, circle or rectangles) of the nodes represent functional classification of the genes shown.

These "top" three networks with p values of <0.05 based on Fisher's exact test were associated with genetic disorder, cellular development, cell death, and cell signaling. Direct interactions between the genes in the network pathways are indicated by solid lines and indirect relationships are indicated by dashed lines. The shaded genes represent the 536 candidate genes identified in the association study described above (85 candidate genes+451 cis-regulatory genes that are associated with the 85 candidate genes).

Example 7

ABCD3 Gene Highly Expressed in AA Metastatic Prostate Cancer Lines

As described above, the association study of 85 candidate genes with genome-wide SNPs in HapMap YRI lymphoblastoid cell lines has revealed an association of SNPs surrounding ABCD3 gene with basal gene expression of RanGAP1 using data obtained from SCAN database (FIG. 1). This variation in expression levels of RanGAP1 might be influenced by the SNPs in ABCD3. To confirm the results obtained during the association study, whether variation in gene expression of ABCD3 influences AA prostate tumors was tested.

Figure 5:
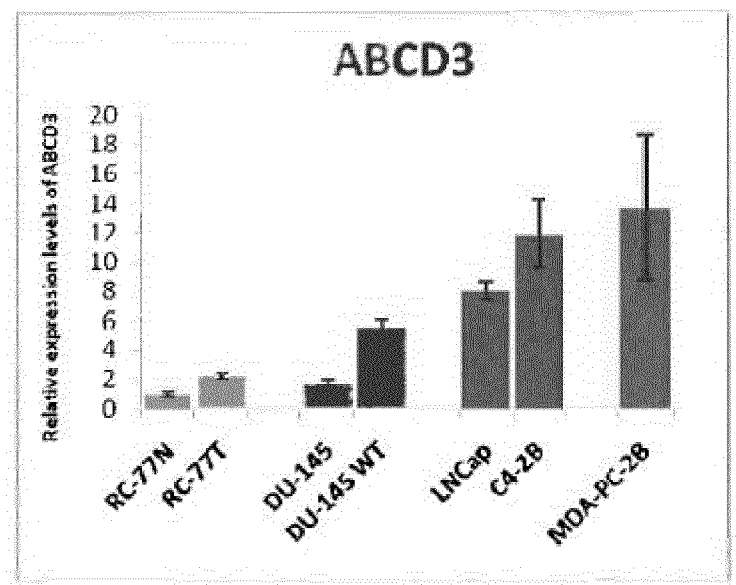
FIG. 5 shows expression of ABCD3 in panel of paired prostate cancer cell lines. (A) qRT-PCR of non-malignant African American RC-77N/E was compared to malignant RC-77T/E cells, DU-145 was compared to DU-145 WT (EGFR overexpressing), LnCaP was compared to C4-2B, and all samples were compared to African American MDA-PC-2b cells. Results shown are representative of experiments performed in triplicate.

Verification of ABCD3 gene in AA/CA prostate cancer cell lines revealed an increase in gene expression with increased metastasis across a novel panel of African American and Caucasian prostate cancer paired cell lines. The malignant RC-77T/E cells isolated from AA showed 2-fold increased expression compared to non-malignant RC-77N matched pair. The metastatic, androgen dependent MDA-2PC-2B cell line derived from AA exhibited a 10-fold ABCD3 expression (FIG. 5). Previously, it has been demonstrated that DU-145 WT (EGFR over-expressing) cells exhibit increased invasiveness and metastasis both in vitro and in vivo[49]. Therefore, ABCD3 gene expression in the DU-145 WT cell and in non-transfected DU-145 cells was examined. DU-145 WT cells showed a 4-fold increase in expression relative to DU-145 prostate cell lines. A similar pattern of expression was observed in the androgen independent metastatic C4-2B cells derived from Caucasian androgen dependent LNCaP cells, thus providing firm evidence of increased ABCD3 gene expression with increased prostate cancer progression in AA tumors (see also FIG. 6).

ABCD3 showed a high probability of being found within three growth factor initiated network hubs involving ERK, MAPK and NFkB proteins. The ERK MAPK has been implicated in a number of pathophysiological events including androgen receptor signaling[58] and the epithelial to mesenchymal EMT[59] that occurs as cancer cells acquire the property to metastasize. That a 4-fold increase in ABCD3 expression in an EGFR over-expressing DU-145 WT cell line compared to non-transfected DU-145 cells (FIG. 6) was observed highlights a putative novel regulator of ABCD3. EGFR is over-expressed in African American Prostate patients[60] and a robust activator of MAPK ERK in normal and cancer cells[61]. Furthermore over-expression is sufficient to increase proliferation, invasion related EMT, and metastasis[49, 62, 63]. Thus, ABCD3 is a novel prostate cancer associated gene that can, in part, be regulated by EGFR signaling.

SNPs identified include:

|  | Pca risk p-value | Pca aggressiveness p-value |
|---|---|---|
| rs1041282 | 0.4901 | 0.7518 |
| rs10493872 | 0.4780 | 0.4735 |
| rs11165135 | 0.7386 | 0.8003 |

-continued

| | Pca risk p-value | Pca aggressiveness p-value |
|---|---|---|
| rs12037634 | 0.6856 | 0.9270 |
| rs17410643 | 0.2184 | 0.3467 |
| rs1749541 | 0.9863 | 0.5447 |
| rs4847303 | 0.6942 | 0.6870 |
| rs582798 | 0.8293 | 0.3723 |
| rs6681849 | 0.2593 | 0.9649 |
| rs724829 | 0.9366 | 0.9010 |

Example 8

RT-PCR Validation in Novel Panel of AA and CA Prostate Cancer Lines

RT-PCR assay was done using a 7500 FAST Real-Time ABI Systems.

Briefly, total RNA from each cultured prostate cell line was extracted separately with RNAxol B (I el-Test Inc., Friedswood, Tx) according to the manufacturer's protocol and quantified with Nucleic Acid Quantitation Kit (NBI, Plymouth, Minn.). Total RNA (1 ug) was reverse transcribed into cDNA with RT2 First strand Kit (SABiosciences/A Qiagen Company), and 1.10 of the reverse-transcribed product from each sample was used for PCR to amplify ABCD3 gene, using a RT2qPCR Primer Assay for Human ABCD3 (SABiosciences/A Qiagen Company). The expression of GAPDH was used as an internal control/housekeeping gene. PCR experimental conditions for the ABCD3 gene were optimized to analyze the amplified product in the linear range of amplification by adjusting amplification cycles for each set of primers. The expected band size (bp) size of the PCR product was 83, the same as described by vendor (SABiosciences). Primers that were used in the example were siRNA ABCD3 gene part #4392421 Assay ID# s229943, Taqman primer part #4331182 Assay ID# Hs00161065_m1, and Taqman control part #4331182 Assay ID# Hs02758991_g1, which were obtained from Applied Biosystems.®

Example 9

Prostate Cancer Cell Lines

Description

Non-malignant (RC-77N/E) and malignant (RC-77T/E) prostate cells were derived from an African American prostate cancer patient and are both androgen sensitive[45]. RC-77N/E cells were isolated from pathological normal cells, while RC-77T/E cells were derived from stage T3 tumor. Both cell lines are cultured in Keratinocyte Serum-Free Medium (KGM) Life Technologies, Gaithersburg, Md., USA), supplemented with bovine pituitary extract (BPE), recombinant epidermal growth factor (rEGF), 1% (v/v) penicillin-streptomycin-neomycin (PSN) antibiotic mixtures and 1% (v/v) amphotericin B (KGM) (Life Technologies, Gaithersburg. Md., USA). MDA-2PC-2B, also derived from an African American patient are androgen dependent, metastatic and are cultured in F12 K medium. DU-145, a cell line originally derived from a brain metastasis of a human prostate adenocarcinoma[46] retains the androgen independence of the original tumor and does not express a functional AR[47]. This cell line has both LHRH-R and epidermal growth factor receptors (EGFR) and produces the EGFR ligands, transforming growth factor-a (TGF-α) and EOF[48,49]. Utilizing established protocols, DU-145 cells were transfected by retroviral-containing EGFR constructs[50]. The wild-type (WT) EGFR construct is a full-length cDNA derived from a placental cDNA library. Cells expressing WT EGFR at levels that escape down-regulation demonstrate enhanced invasiveness in vitro[51]. LNCaP cells were derived from a lymph node metastasis[52]. The Caucasian LNCaP, C42-B prostate cancer cell lines were maintained in T-medium as previously described.

Example 10

Determine Expression of ABCD3 in AA and in CA Prostate Tumors/and in AA/CA BMP Tissue To provide evidence hypothesis that AA CaP tumors exhibit higher expression of ABCD3 than CA tumors, IHC methods will be used to detect the expression of ABCD3 in archival formalin fixed paraffin embedded (FFPE) prostate tissue of grades >7 and of grades <7. Benign hyperplasia prostate FFPE samples from AA and CA will serve as controls. RNA Interference and functional genomics can also be used. Cell lines such as RC77N/E (non-malignant), RC-77T/E (malignant), MDA-2Pca-2b derived from AA are androgen dependent and metastatic; PC-3 derived from Caucasians are androgen dependent; PrEC are non-malignant prostate epithelial cells derived from a Caucasian male; and RC92a/h TERT cells derived from malignant prostate tumors of a Caucasian male can be used.

Example 11

Expression of ABCD3 Protein Levels in Prostate Tumors

Figure 6:
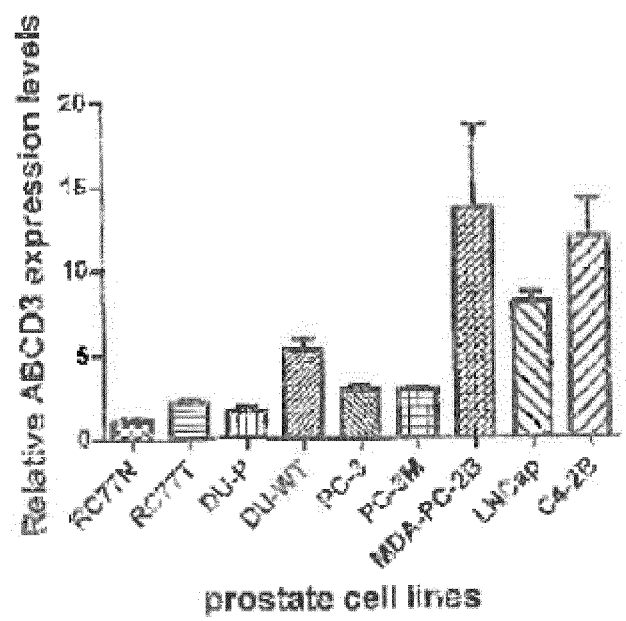
FIG. 6 shows expression of ABCD3 in panel of paired prostate cancer cell lines.

Expression of ABCD3 in human prostate tumor tissue was examined using an antibody specific for ABCD3 polypeptide. See FIG. 7, A-H, where human prostate tumor tissue (A thru D), normal adjacent tissue (E &F) and normal or non-tumor prostate tissue (G & H) is shown. Expression levels were classified as negative, weakly positive or strong positive. Representative immunostaining photographs showed that strong positive immunoreactivity of ABCD3 was detected in prostate tumors of Grade 1, 2, 3 and 4 (FIG. 6, A thru D). The intensity of expression appeared to be much greater in Grade 4 prostate tumor tissue (D) as depicted by the extensive brown staining for strong positive ABCD3 expression compared to the intensity observed in Grades 1 thru 3. The location of the ABCD3 expressed polypeptide is in the cytoplasm and in the membrane of seminal vesicle (the open white areas seen in A and B are seminal vesicles). Weak positive or low intensity staining of ABCD3 was observed in non-tumor tissue (G and H); however positive staining was evident in normal adjacent tissue (E and F). In summary, The overall expression of ABCD3 was much greater in advanced prostate tumors relative to non-tumor and normal adjacent tissues.

IHC Staining of Human Prostate Cancer Tissue Array

Materials

The tissue microarray used for this study was human prostate cancer tissue array PR2085b. PR2085b contains 92 cases of adenocarcinoma, 2 cases of prostate transitional cell carcinoma, 12 cases of prostate adjacent normal tissues and 8 cases of normal prostate tissue samples. The array is in duplicate cores per case format. The tissue samples were formalin fixed, paraffin embedded. Tissue array sections were mounted on the positive charged SuperFrost Plus glass slide. The tissue microarray sections were cut at 5 micron in thickness. Individual cores were 1.0 mm in diameter, spaced 0.25 mm.

Primary antibody—rabbit anti-ABCD3 antibody was purchased from Sigma-Aldrich (Catalog #: HPA 032027). Antibody concentration was 70 µg/ml.

ImmPRESS™ Reagent anti-Rabbit Ig (peroxidase), catalog number MP7401, was purchased from Vector Laboratories. DAB (DAKO Cytomation, Code K3465) used as substrate chromogen. Antigen retrieval solution was purchased from DakoCytomation (Target Retrieval solution, S-1699). The Antigen retrieval was performed before incubating with primary antibody.

Staining Procedure

1. Deparaffinize and hydrate tissue section through xylene and gradient ethanol series.
2. Rinse for 5 minutes in water.
3. Incubate the sections for 5 minutes in 3% H2O2 in water to block endogenous peroxidase.
4. Wash in water for 5 minutes 2 times.
5. Antigen retrieval by using 1× antigen retrieval solution, 20 minutes in microwave oven with simmering conditions. Cool down in room temperature for 15 minutes.
6. Wash slide for 3×5 minutes in PBST buffer.
7. Incubate section for 30 minutes with ready-to-use (2.5%) normal horse blocking serum.
8. Incubate sections with primary antibody diluted with antibody Diluent for 1 hour at room temperature. Antibody dilutions were 1:75 (0.93 µg/ml) and 1:225 (0.31 µg/ml).
9. Wash slides for 3×5 minutes in buffer.
10. Incubate sections for 30 minutes with ImmPRESS™ reagent.
11. Wash slides for 3×5 minutes in buffer.
12. Incubate sections in peroxidase substrate DAB solution.
13. Rinse sections in tap water.
14. Counterstain the slide with Hematoxylin QS (Vector Labs, H-3404).
15. Clear and mount with permanent mounting medium (C0487, Sigma).

Experiment Notes

In IHC procedures, the DAB substrate-chromogen yields a dark brown reaction end-product at the site of the target antigen. Hematoxylin was used for counterstaining cell nuclei which yields blue color staining.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

REFERENCES

1. American Cancer Society Facts and Figures (2008). Atlanta: American Cancer Society.
2. Powell I J (1997). Keynote address: prostate cancer among African-American men—from the bench to the community. Prostate cancer and African-American men. Oncology (Williston Park), 11(5):599-605; discussion 606-15 passim. Review. PMID: 9159788.
3. Powell I J (1998). Prostate cancer in the African American: is this a different disease? Semin Urol Oncol., 16(4):221-6. Review. PMID: 9858329.
4. Giovannucci E, Platz E A, Stampfer M J, Chan A, Krithivas K, Kawachi I, et al, (1999). The CAG repeat within the androgen receptor gene and benign prostatic hyperplasia. Urology. 53:121-5. doi:10.1016/S0090-4295(98)00468-3.
5. Caskey C T, Pizzuti A, Fu Y H, Fenwick R G Jr, Nelson D L (1992). Triplet repeat mutations in human disease. Science, 256(5058):784-9. doi:10.1126/science.1589758.
6. Platz E A, Rimm E B, Willett W C, Kantoff P W, Giovannucci E (2000). Racial variations in prostate cancer incidence and in hormonal system markers among male health professionals. J Natl Cancer Inst., 92(24):2009-17. doi:10.1093/jnci/92.24.2009.
7. Smith G E, DeHaven M J, Grundig J P. Wilson G R (1997). African-American males and prostate cancer: assessing knowledge levels in the community. J Natl Med Assoc., 89(6):387-91.
8. Barber K R, Shaw R. Folts M, Taylor D K, Ryan A, Hughes M, et al., (1998). Differences between African-American and Caucasian men participating in a community-based prostate cancer screening program. J Community Health, 23(6):441-51. doi:10.1023/A:1018758124614.
9. Abbott R R, Taylor D K, Barber K (1998). A comparison of prostate knowledge of African-American and Caucasian men: Changes from prescreening baseline to post-intervention. Cancer J Sci Am., 4(3):175-7.
10. Steele C B. Miller D S, Maylahn C, Uhler R J, Baker C T (2000). Knowledge, attitudes, and screening practices among older men regarding prostate cancer. Am J Public Health, 90(10):1595-600.
11. Agho A O, Lewis M A (2001). Correlates of actual and perceived knowledge of prostate cancer among African Americans. Cancer Nurs., 24(3):165-71. doi:10.1097/00002820-200106000-00001.
12. Ashford A R, Albert S M, Hoke G, Cushman L F, Miller D S, Bassett M (2001). Prostate carcinoma knowledge, attitudes, and screening behavior among African-American men in Central Harlem, New York City. Cancer, 91(1):164-72. doi:10.1002/1097-0142(20010101)91:1<164::AID-CNCR21>3.0.CO; 2-A.
13. Magnus M (2004). Prostate cancer knowledge among multiethnic black men. J Natl Med Assoc., 96(5):650-6.
14. Richardson J T, Webster J D, Fields N J (2004). Uncovering myths and transforming realities among low-SES African-American men: Implications for reducing prostate cancer disparities. J Natl Med Assoc., 96(10):1295-302.
15. Woods V D, Montgomery S B, Belliard J C, Ramirez-Johnson J, Wilson C M (2004). Culture, black men, and prostate cancer: What is reality? Cancer Control, 11(6): 388-96.
16. Forrester-Anderson I T (2005). Prostate cancer screening perceptions, knowledge, and behaviors among African American men: Focus group findings. J Health Care Poor Underserved, 16(4, Suppl A):22-30. doi:10.1353/hpu.2005.0122.
17. Jones A R, Shipp M, Thompson C J, Davis M K (2005). Prostate cancer knowledge and beliefs among black and white older men in rural and urban counties. J Cancer Educ, 20:96-102. doi:10.1207/s15430154jce2002_10.
18. Ross L E, Uhler R J, Williams K N (2005). Awareness and use of prostate-specific antigen test among African-American men. J Natl Med Assoc., 97(7):963-71.
19. Pruthi R S, Tornehl C, Gaston K, Lee K, Moore D, Carson C C, et al., (2006). Impact of race, age, income, and residence on prostate cancer knowledge, screening behavior, and health maintenance in siblings of patients with prostate cancer. Eur Urol., 50(1):64-9. doi:10.1016/j.eururo.2005.09.024.
20. McWhorter W B, Schatzkin A G, Horm J W, Brown C C (1989). Contribution of socioeconomic status to Black/

White differences in cancer incidence. Cancer, 63:982-7. doi:10.1002/1097-0142(19890301)63:5<982::AID-CNCR2820630533>3.0.CO;2-1.
21. Baguet C R, Horm J W, Gibbs T, Greewald P (1991). Socioeconomic factors and cancer incidence among Blacks and Whites. J Natl Cancer Inst., 83:551-7. doi: 10.1093/jnci/83.8.551.
22. Robbins A S, Whittemore A S, Van Den Eeden S K (1989). Race, prostate cancer survival, and membership in a large health maintenance organization. J Natl Cancer Inst., 90(13):986-90. doi:10.1093/jnci/90.13.986.
23. Brawn P N, Johnson E H, Kuhl D L, Riggs M W, Speights V O, Johnson C F III, et al., (1993). Stage at presentation and survival of white and black patients with prostate carcinoma. Cancer. 71(8):2569-73. doi:10.1002/1097-0142(19930415)71:8<2569::AID-CNCR2820710822>3.0.CO;2-R.
24. Ndubuisi S C, Kofie V Y, Andoh J Y, Schwartz E M (1995). Black-white differences in the stage at presentation of prostate cancer in the District of Columbia. Urology., 46(1):71-7. doi:10.1016/S0090-4295(99)80162-9.
25. Freedland S J, Amling C L, Dorey F, Kane C J, Presti J C, Terris M K, et al., (2002). Race as an outcome predictor following radical prostatectomy: Results from the Shared Equal Access Regional Cancer Hospital (SEARCH) Database. Urology, 60:670-4. doi:10.1016/50090-4295(02)01847-2.
26. Polednak A P, Flannery J T (1992). Black versus white racial differences in clinical stage at diagnosis and treatment of prostatic cancer in Connecticut. Cancer, 70:2152-8. doi: 10.1002/1097-0142(19921015)70:8<2152::AID-CNCR2820700824>3.0.CO;2-#.
27. Moul J W, Sesterhenn I A, Connelly R R, Douglas T, Srivastava S, Mostofi F K, et al., (1995). Prostate-specific antigen values at the time of prostate cancer diagnosis in African American men. J Am Med Assoc., 274:1277-81.
28. Horner R D (1998). Racial variation in cancer care: A case study of prostate cancer. Cancer Treat Res., 97:99-114. doi:10.1007/978-0-585-30498-48.
29. Brawley O W, Knopf K, Thompson I (1998). The epidemiology of prostate cancer part II: The risk factors. Semin Urol Oncol., 16:193-201.
30. Fowler J E Jr, Bigler S, Bowman G, Kilambi N (2000). Race and cause specific survival with prostate cancer: Influence of clinical stage, Gleason score, age and treatment. J Urol, 163(1):137-42. doi:10.1016/S0022-5347(05)67989-X.
31. Whittemore A S, Kolonel L N, Wu A H, John E M, Gallagher R P, Howe G R, et. al., (1995). Prostate cancer in relation to diet, physical activity, and body size in blacks, whites, and Asians in the United States and Canada. J Natl Cancer Inst., 87(9):652-61. doi:10.1093/jnci/87.9.652.
32. Freedland S J, Isaacs W B (2005). Explaining racial differences in prostate cancer in the United States Sociology or biology? Prostate, 62:243-52. doi:10.1002/pros.20052.
33. Guo Y, Sigman D B, Borkowski A, Kyprianou N (2000). Racial differences in prostate cancer growth: Apoptosis and cell proliferation in Caucasian and African-American patients. Prostate, 42:130-6. doi:10.1002/(SICI) 1097-0045(20000201)42:2<130::AID-PROS7>3.0.CO; 2-3.
34. Ross R, Bernstein L, Judd H, Hanisch R, Pike M, Henderson B (1986). Serum testosterone levels in healthy young black and white men. J Natl Cancer Inst, 76:45-8.
35. Ross R, Bernstein L, Lobo R A, Shimizu H, Stanczyk F Z, Pike M C, et. al., (1999). 5-alpha-reductase activity and risk of prostate cancer among Japanese and US White and Black males. Lancet., 339:887-9. doi:10.1016/0140-6736(92)90927-U.
36. Reams, R. R.; Agrawal, D.; Davis, M.; Yoder. S.; Odedina. F.; Kumar, N.; Higginbotham, J.; Akinremi, T.; Suther, S.; Soliman, K., (2009). Microarray comparison of prostate tumor gene expression in African-American and Caucasian American males: a pilot project study. Infectious Agents and Cancer, 4, (Suppl 1), S3.
37. Wallace, T. A.; Prueitt, R. L.; Yi, M.; Howe, T. M.; Gillespie, J. W.; Yfantis, H. G.: Stephens, R. M.; Caporaso, N. E.; Loffredo, C. A.; Ambs, S., (2008). Tumor Immunobiological Differences in Prostate Cancer between African-American and European-American Men. Cancer Res, 68, (3), 927-936.
38. Timofeeva O A, Zhang X, Ressom H W, Varghese R S, Kallakury B V, Wang K, Ji Y, Cheema A, Jung M, Brown M L, Rhim J S, Dritschilo A. (2009). Enhanced expression of SOS1 is detectable in prostate cancer epithelial cells from African-American men. Int J Oncol. 2009 October; 35(4): 751-60.
39. Gamazon E R, Zhang W, Konkashbaev A, Duan S, Kistner E O, Nicolae D L, Dolan M E, Cox N J. (2010) SCAN: SNP and copy number annotation. Bioinformatics. 2010 Jan. 15; 26(2):259-62. Epub 2009 Nov. 17. PMID: 19933162 [PubMed—indexed for MEDLINE]
40. Nicolae D L, Gamazon E, Zhang W, Duan S, Dolan M E, and Cox N J. (2010) Trait-Associated SNPs Are More Likely to Be eQTLs: Annotation to Enhance Discovery from GWAS. PLoSGenet 6(4): e1000888. doi: 10.1371/journal.pgen. 1000888 PMID 20369019
41. Gamazon, E. R., Zhang W., Konkashbaev A., Duan S., Kistner E., Nicolae D. L., Dolan, M. E., Cox, N. J. SCAN: SNP and copy number annotation. Bioinformatics Advance Access published on Nov. 17, 2009, doi:10.1093/bioinformatics/btp644 PMID 19933162
42. Duan, S., Huang, R. S., Zhang, W., Bleibel, W. K., Roe, C. A., Clark, T. A., Chen, T. X., Schweitzer, A. C., Blume, J. E., Cox, N. J., and Dolan, M. E. Genetic Architecture of Transcript-Level Variation in Humans. Amer. J. Human Genetics, 82:1101-1113, 2008. PMID 18439551
43. Zhang, W., Duan, S., Kistner, E. O., Bleibel, W. K., Huang, R. S., Clark, T. A., Chen, T. X., Schweitzer, A. C., Blume, J. E., Cox, N. J. and Dolan, M. E. Evaluation of Genetic Variation Contributing to Differences in Gene Expression Between Populations. Amer. J. Human Genetics, 82: 631-640, 2008. PMID 18313023
44. Duan S, Zhang W, Bleibel W K, Cox N J, Dolan M E. SNPinProbe_1.0: A database for filtering out probes in the Affymetrix GeneChip(R) Human Exon 1.0 ST array potentially affected by SNPs. Bioinformation 2(10):469-70, 2008. PMID 18841244
45. Theodore S, Sharp S, Zhou J, et al. Establishment and characterization of a pair of non-malignant and malignant tumor derived cell lines from an African American prostate cancer patient. International journal of oncology; 37: 1477-82.
46. Stone K R, Mickey D D, Wunderli H, Mickey G H, Paulson D F. Isolation of a human prostate carcinoma cell line (DU 145). International journal of cancer 1978; 21:274-81.
47. Dondi. D., et al., Growth-inhibitory effects of luteinizing hormone-releasing hormone (LHRH) agonists on xenografts of the DU 145 human androgen-independent prostate cancer cell line in nude mice. Int J Cancer. 1998. 76(4): p. 506-11.

48. Jungwirth A, Pinski J, Galvan G, et al Inhibition of growth of androgen-independent DU-145 prostate cancer in vivo by luteinising hormone-releasing hormone antagonist Cetrorelix and bombesin antagonists RC-3940-II and RC-3950-II. Eur J Cancer 1997; 33: 1141-8.
49. Turner T, Chen P, Goodly L J, Wells A. EGF receptor signaling enhances in vivo invasiveness of DU-145 human prostate carcinoma cells. Clinical & experimental metastasis 1996; 14: 409-18.
50. Wells A, Welsh J B, Lazar C S, Wiley H S, Gill G N, Rosenfeld M G. Ligand-induced transformation by a non-internalizing epidermal growth factor receptor. Science. 1990:247:962-964.
51. Xie H, Turner T, Wang M H, Singh R K, Siegal G P, Wells A., 1996. In Vitro invasiveness of DU-145 human prostate carcinoma cells is modulated by EGF receptor-mediated signals. Clin Exp Metastasis. 1995 November; 13(6):407-19.
52. Horoszewicz, J. S., et al., The LNCaP cell line—a new model for studies on human prostatic carcinoma. Prog Clin Biol Res, 1980. 37: p. 115-32.
53. Tusher V G, Tibshirani R., Chu G. Significance analysis of micro arrays applied to the Ionizing radiation response. Proc Nation Acad Sci USA 2001, 98(9): 5116-21.
54. Odedina F T, Akinremi T O, Chinegwundoh F, Roberts R, Yu D, Reams R R, Freedman M L, Rivers B, Green B L, Kumar N. (2009). Prostate cancer disparities in Black men of African descent: a comparative literature review of prostate cancer burden among Black men in the United States, Caribbean, United Kingdom, and West Africa, Infect Agent Cancer. 10; 4 Suppl 1:S2.
55. Liu Y, Peng H, Zhang J T. Expression profiling of ABC transporters in a drug-resistant breast cancer cell line using AmpArray. Mol Pharmacol 2005; 68: 430-8.
56. Huss W J, Gray D R, Greenberg N M, Mohler J L, Smith G J. Breast cancer resistance protein-mediated efflux of androgen in putative benign and malignant prostate stem cells. Cancer research 2005; 65: 6640-50.
57. Theodore S C, Rhim J S, Turner T, Yates C. MiRNA 26a expression in a novel panel of African American prostate cancer cell lines. Ethn Dis; 20: S1-96-100.
58. Peterziel H, Mink S, Schonert A, Becker M, Klocker I I, Cato A C. Rapid signalling by androgen receptor in prostate cancer cells. Oncogene 1999; 18: 6322-9.
59. Odero-Marah V A, Wang R, Chu G, et al. Receptor activator of NF-kappaB Ligand (RANKL) expression is associated with epithelial to mesenchymal transition in human prostate cancer cells. Cell Res 2008; 18: 858-70
60. Shuch B, Mikhail M, Satagopan J, et al. Racial disparity of epidermal growth factor receptor expression in prostate cancer. J Clin Oncol 2004; 22: 4725-9.
61. Gan Y, Shi C, Inge L, Hibner M, Balducci J, Huang Y. Differential roles of ERK and Akt pathways in regulation of EGFR-mediated signaling and motility in prostate cancer cells. Oncogene; 29: 4947-58.
62. Yates C, Wells A, Turner T. Luteinising hormone-releasing hormone analogue reverses the cell adhesion profile of EGFR overexpressing DU-145 human prostate carcinoma subline. British journal of cancer 2005; 92: 366-
63. Yates C C, Shepard C R, Stolz D B, Wells A. Co-culturing human prostate carcinoma cells with hepatocytes leads to increased expression of E-cadherin. British journal of cancer 2007; 96: 1246-52.
64. Theodore, S., Sharp, S., Zhou, J., Turner T., Yates, C, Rhim, J. 2010 "Establishment of a Novel non-malignant and malignant cell line paired cell line from African American Prostate Cancer Patient." Int. J. Oncol. December; 37(6): 1477-82.
65. Theodore, S., Turner T., Rhim. J., Yates, C. 2010 "miRNA 26a Expression in a Novel Panel of African American Prostate Cancer Cell Lines" Ethnicity and Disease Volume 20, Suppl 1, Pages S1-96-100 PMID 20521394.
66. Gamazon E R, Zhang W., Huang R S, Dolan M E, Cox N J (2010) A pharmacogene database enhanced by the 1000 Genomes Project. Pharmacogenet Genomics. 2009 October; 19(10):829-32. PMID: 19745786.

TABLE 1

| From | Entrez gene ID | David Gene Name |
|---|---|---|
| ARPC1A | 10552 | ACTIN RELATED PROTEIN 2/3 COMPLEX, SUBUNIT 1A, 41KDA |
| ADAMTS6 | 11174 | ADAM METALLOPEPTIDASE WITH THROMBOSPONDIN TYPE 1 MOTIF, 6 |
| AGXT | 189 | ALANINE-GLYOXYLATE AMINOTRANSFERASE (OXALOSIS I; HYPEROXALURIA I; GLYC . . . |
| ANK2 | 287 | ANKYRIN 2, NEURONAL |
| A2BP1 | 54715 | ATAXIN 2-BINDING PROTEIN 1 |
| TPPP | 11076 | BRAIN-SPECIFIC PROTEIN P25 ALPHA |
| BXDC2 | 55299 | BRIX DOMAIN CONTAINING 2 |
| BUB3 | 9184 | BUB3 BUDDING UNINHIBITED BY BENZIMIDAZOLES 3 HOMOLOG (YEAST) |
| CTNND1 | 1500 | CATENIN (CADHERIN-ASSOCIATED PROTEIN), DELTA 1 |
| CSPP1 | 79848 | CENTROSOME AND SPINDLE POLE ASSOCIATED PROTEIN 1 |
| CXCL2 | 2920 | CHEMOKINE (C-X-C MOTIF) LIGAND 2 |
| CHRNA10 | 57053 | CHOLINERGIC RECEPTOR, NICOTINIC, ALPHA 10 |
| C10ORF53 | 282966 | CHROMOSOME 10 OPEN READING FRAME 53 |
| C15ORF26 | 161502 | CHROMOSOME 15 OPEN READING FRAME 26 |
| C21ORF88 | 114041 | CHROMOSOME 21 OPEN READING FRAME 88 |
| C6ORF105 | 84830 | CHROMOSOME 6 OPEN READING FRAME 105 |
| C9ORF62 | 157927 | CHROMOSOME 9 OPEN READING FRAME 62 |
| C9ORF93 | 203238 | CHROMOSOME 9 OPEN READING FRAME 93 |
| CNTN4 | 152330 | CONTACTIN 4 |
| CPEB4 | 80315 | CYTOPLASMIC POLYADENYLATION ELEMENT BINDING PROTEIN 4 |
| DDX19B | 55308 | DEAD (ASP-GLU-ALA-AS) BOX POLYPEPTIDE 19B |
| DDX19B | 11269 | DEAD (ASP-GLU-ALA-AS) BOX POLYPEPTIDE 19B |
| DDX19B | 544314 | DEAD (ASP-GLU-ALA-AS) BOX POLYPEPTIDE 19B |

TABLE 1-continued

| From | Entrez gene ID | David Gene Name |
|---|---|---|
| DAD1 | 1603 | DEFENDER AGAINST CELL DEATH 1 |
| DLL3 | 10683 | DELTA-LIKE 3 (*DROSOPHILA*) |
| DIRAS2 | 54769 | DIRAS FAMILY, GTP-BINDING RAS-LIKE 2 |
| DOT1L | 84444 | DOT1-LIKE, HISTONE H3 METHYLTRANSFERASE (*S. CEREVISIAE*) |
| GPR12 | 2835 | G PROTEIN-COUPLED RECEPTOR 12 |
| GATA4 | 2626 | GATA BINDING PROTEIN 4 |
| GPC5 | 2262 | GLYPICAN 5 |
| HES4 | 57801 | HAIRY AND ENHANCER OF SPLIT 4 (*DROSOPHILA*) |
| HELB | 92797 | HELICASE (DNA) B |
| HNRPD | 3184 | HETEROGENEOUS NUCLEAR RIBONUCLEOPROTEIN D (AU-RICH ELEMENT RNA BINDING . . . |
| HDAC11 | 79885 | HISTONE DEACETYLASE 11 |
| HOXB5 | 3215 | HOMEOBOX B5 |
| HOXD4 | 3233 | HOMEOBOX D4 |
| FLJ44606 | 401207 | HYPOTHETICAL GENE SUPPORTED BY AK126569 |
| INSC | 387755 | HYPOTHETICAL PROTEIN |
| DKFZP547J222 | 84237 | HYPOTHETICAL PROTEIN DKFZP547J222 |
| FLJ30934 | 254122 | HYPOTHETICAL PROTEIN FLJ30934 |
| FLJ32658 | 147872 | HYPOTHETICAL PROTEIN FLJ32658 |
| LOC285857 | 285857 | HYPOTHETICAL PROTEIN LOC285857 |
| LOC440295 | 374676 | HYPOTHETICAL PROTEIN LOC374676 |
| LOC440295 | 440295 | HYPOTHETICAL PROTEIN LOC374676 |
| ITGB6 | 3694 | INTEGRIN, BETA 6 |
| IRF4 | 3662 | INTERFERON REGULATORY FACTOR 4 |
| LRRC28 | 123355 | LEUCINE RICH REPEAT CONTAINING 28 |
| LIPC | 3990 | LIPASE, HEPATIC |
| GPR98 | 84059 | MONOGENIC, AUDIOGENIC SEIZURE SUSCEPTIBILITY 1 HOMOLOG (MOUSE) |
| MOBP | 4336 | MYELIN-ASSOCIATED OLIGODENDROCYTE BASIC PROTEIN |
| MLL4 | 9757 | MYELOID/LYMPHOID OR MIXED-LINEAGE LEUKEMIA 4 |
| NCR3 | 259197 | NATURAL CYTOTOXICITY TRIGGERING RECEPTOR 3 |
| NSFL1C | 55968 | P47 (RAT) |
| PAX5 | 5079 | PAIRED BOX GENE 5 (B-CELL LINEAGE SPECIFIC ACTIVATOR) |
| PITX1 | 5307 | PAIRED-LIKE HOMEODOMAIN TRANSCRIPTION FACTOR 1 |
| KCNQ5 | 56479 | POTASSIUM VOLTAGE-GATED CHANNEL, KQT-LIKE SUBFAMILY, MEMBER 5 |
| PGR | 5241 | PROGESTERONE RECEPTOR |
| PDCD1 | 5133 | PROGRAMMED CELL DEATH 1 |
| RANGAP1 | 5905 | RAN GTPASE ACTIVATING PROTEIN 1 |
| REEP3 | 221035 | RECEPTOR ACCESSORY PROTEIN 3 |
| RNF168 | 165918 | RING FINGER PROTEIN 168 |
| RNF187 | 149603 | RING FINGER PROTEIN 187 |
| SSH1 | 54434 | SLINGSHOT HOMOLOG 1 (*DROSOPHILA*) |
| SLC13A2 | 9058 | SOLUTE CARRIER FAMILY 13 (SODIUM-DEPENDENT DICARBOXYLATE TRANSPORTER), . . . |
| SLC4A9 | 83697 | SOLUTE CARRIER FAMILY 4, SODIUM BICARBONATE COTRANSPORTER, MEMBER 9 |
| SLC6A15 | 55117 | SOLUTE CARRIER FAMILY 6, MEMBER 15 |
| SPATA12 | 353324 | SPERMATOGENESIS ASSOCIATED 12 |
| SFRS1 | 6426 | SPLICING FACTOR, ARGININE/SERINE-RICH 1 (SPLICING FACTOR 2, ALTERNATE . . . |
| ST6GALNAC3 | 256435 | ST6 (ALPHA-N-ACETYL-NEURAMINYL-2,3-BETA-GALACTOSYL-1,3)-N-ACETYLGALACT . . . |
| STXBP2 | 6813 | SYNTAXIN BINDING PROTEIN 2 |
| TNIK | 23043 | TRAF2 AND NCK INTERACTING KINASE |
| TCF12 | 6938 | TRANSCRIPTION FACTOR 12 (HTF4, HELIX-LOOP-HELIX TRANSCRIPTION FACTORS . . . |
| TCF3 | 6929 | TRANSCRIPTION FACTOR 3 (E2A IMMUNOGLOBULIN ENHANCER BINDING FACTORS E1 . . . |
| TRPM7 | 54822 | TRANSIENT RECEPTOR POTENTIAL CATION CHANNEL, SUBFAMILY M, MEMBER 7 |
| TMEM67 | 91147 | TRANSMEMBRANE PROTEIN 67 |
| TMEM74 | 157753 | TRANSMEMBRANE PROTEIN 74 |
| TRMT1 | 55621 | TRM1 TRNA METHYLTRANSFERASE 1 HOMOLOG (*S. CEREVISIAE*) |
| TTLL5 | 23093 | TUBULIN TYROSINE LIGASE-LIKE FAMILY, MEMBER 5 |
| TPST1 | 8460 | TYROSYLPROTEIN SULFOTRANSFERASE 1 |
| UBE2U | 148581 | UBIQUITIN-CONJUGATING ENZYME E2U (PUTATIVE) |
| WDR1 | 9948 | WD REPEAT DOMAIN 1 |
| WDR32 | 79269 | WD REPEAT DOMAIN 32 |
| WDR60 | 55112 | WD REPEAT DOMAIN 60 |
| ZNF75 | 7626 | ZINC FINGER PROTEIN 75 (D8C6) |
| ZFAND5 | 7763 | ZINC FINGER, A20 DOMAIN CONTAINING 2 |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of determining an increased likelihood of prostate cancer cells to metastasize in a subject,
    comprising detecting in a prostate cancer cell sample from a subject, an increased level of an ABCD3 polypeptide compared to the level of an ABCD3 polypeptide from a control,
    wherein the control comprises non-cancerous prostate cells,
    the increased level of an ABCD3 polypeptide in the sample from the subject being indicative of an increased likelihood of prostate cancer cells in the subject to metastasize,
    wherein the sample is prostate gland tissue.

2. The method of claim 1, wherein the non-cancerous prostate cells comprise low grade cancer cells.

3. The method of claim 1, wherein the non-cancerous prostate cells comprise non-metastatic cells.

4. The method claim of 1, wherein the subject is a mammal.

5. The method of claim 1, wherein the subject is a human.

6. The method of claim 1, wherein the ABCD3 polypeptide is encoded by ABCD3 mRNA.

\* \* \* \* \*